US011276297B2

(12) United States Patent
Worthington et al.

(10) Patent No.: US 11,276,297 B2
(45) Date of Patent: *Mar. 15, 2022

(54) SYSTEMS AND METHODS FOR ROBUST MAN-DOWN ALARMS

(71) Applicant: Honeywell International Inc., Morris Plains, NJ (US)

(72) Inventors: Stephen David Worthington, Calgary (CA); Jerry Wayne Evans, Houston, TX (US); Patrick Gerard Hogan, Vernon Hills, IL (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/883,582

(22) Filed: May 26, 2020

(65) Prior Publication Data

US 2020/0357264 A1 Nov. 12, 2020

Related U.S. Application Data

(62) Division of application No. 13/015,327, filed on Jan. 27, 2011, now Pat. No. 10,685,554.

(51) Int. Cl.
*G08B 25/00* (2006.01)
*G08B 21/04* (2006.01)
(Continued)

(52) U.S. Cl.
CPC ......... *G08B 25/002* (2013.01); *G08B 21/043* (2013.01); *G08B 21/0446* (2013.01);
(Continued)

(58) Field of Classification Search
CPC .. G08B 25/002; G08B 25/00; G08B 21/0446; G08B 21/04; G08B 21/0492;
(Continued)

(56) References Cited

U.S. PATENT DOCUMENTS

| 4,468,656 A | 8/1984 | Clifford et al. |
| 4,665,385 A | 5/1987 | Henderson |

(Continued)

FOREIGN PATENT DOCUMENTS

| BR | 102012001686 A2 | 6/2015 |
| CA | 2765328 A1 | 7/2012 |

(Continued)

OTHER PUBLICATIONS

BR Office Action dated Dec. 16, 2019 for BR Application No. 102012001686.

(Continued)

*Primary Examiner* — Nay Tun
(74) *Attorney, Agent, or Firm* — Alston & Bird LLP

(57) ABSTRACT

A system including at least one detector and a central station in two-way communication with the detector is provided. The detector can include an ambient condition sensing element, a motion sensor, control circuitry, and two-way communications hardware. The control circuitry can determine an alarm event based on a first signal received from the ambient condition sensing element and can transmit an alarm signal to the communications hardware during the alarm event. The control circuitry can also determine a man-down event based on a second signal received from the motion sensor and transmit a man-down alarm signal to the communications hardware during the man-down event. The two-way communications hardware can transmit at least one of the gas alarm signal and the man-down alarm signal to a remote location, and the two-way communications hardware can receive a status inquiry from the remote location.

13 Claims, 6 Drawing Sheets

(51) Int. Cl.
*G08B 29/18* (2006.01)
*G08B 21/12* (2006.01)
*G08B 25/01* (2006.01)

(52) U.S. Cl.
CPC ......... *G08B 21/0492* (2013.01); *G08B 21/12* (2013.01); *G08B 25/016* (2013.01); *G08B 29/188* (2013.01)

(58) Field of Classification Search
CPC .... G08B 21/043; G08B 29/188; G08B 29/18; G08B 21/12; G08B 25/016; G08B 25/01; G08B 19/00; G08B 25/10; A61B 5/1117; A61B 5/11; A61B 5/0024; A61B 5/00
See application file for complete search history.

(56) References Cited

U.S. PATENT DOCUMENTS

| | | |
|---|---|---|
| 4,747,120 A | 5/1988 | Foley |
| 5,045,839 A | 9/1991 | Ellis et al. |
| 5,483,222 A | 1/1996 | Tice |
| 5,862,803 A | 1/1999 | Besson et al. |
| 6,023,223 A | 2/2000 | Baxter, Jr. |
| 6,121,881 A | 9/2000 | Bieback et al. |
| 6,199,550 B1 | 3/2001 | Wiesmann et al. |
| 6,847,892 B2 | 1/2005 | Zhou et al. |
| 7,263,379 B1 | 8/2007 | Parkulo et al. |
| 7,538,666 B2 | 5/2009 | Campman |
| 8,330,605 B2 | 12/2012 | Johnson et al. |
| 2004/0017300 A1 | 1/2004 | Kotzin et al. |
| 2004/0021569 A1 | 2/2004 | Lepkofker et al. |
| 2006/0282021 A1 | 12/2006 | Devaul et al. |
| 2007/0205861 A1 | 9/2007 | Nair et al. |
| 2008/0061962 A1 | 3/2008 | Campman |
| 2008/0211668 A1 | 9/2008 | Dixon et al. |
| 2010/0081411 A1 | 4/2010 | Montenero |
| 2011/0037599 A1* | 2/2011 | Johnson, Jr ........ G08B 13/2462 340/632 |
| 2012/0194334 A1 | 8/2012 | Worthington |
| 2012/0286949 A1 | 11/2012 | Worthington et al. |

FOREIGN PATENT DOCUMENTS

| | | |
|---|---|---|
| CN | 1111380 A | 11/1995 |
| CN | 102622853 B | 9/2016 |
| EP | 2482264 A2 | 8/2012 |
| IN | 219/DEL/2012 | 6/2015 |
| JP | 57-076685 A | 5/1982 |
| JP | 03-073096 A | 3/1991 |
| JP | 06-180790 A | 6/1994 |
| JP | 08-315277 A | 11/1996 |
| JP | 10-011686 A | 1/1998 |
| JP | 2000-339571 A | 12/2000 |
| JP | 2008-015659 A | 1/2008 |
| JP | 2008-198044 A | 8/2008 |
| JP | 2010-056895 A | 3/2010 |
| JP | 5788339 B2 | 9/2015 |
| RU | 72778 U1 | 4/2008 |
| RU | 2401947 C2 | 10/2010 |
| RU | 2606236 C2 | 1/2017 |
| WO | 00/07157 A1 | 2/2000 |
| WO | 2007/057692 A2 | 5/2007 |

OTHER PUBLICATIONS

BR Office Action dated Jul. 19, 2019 for BR Application No. 102012001686.
CA Office Action dated Nov. 13, 2018 for CA Application No. 2765328.
CA Office Action dated Oct. 22, 2019 for CA Application No. 2765328.
Canada Patent Application No. 2765328, Examiner Requisition, dated Nov. 11, 2017, 6 pages.
China Patent Application No. 201210063759.5, First Office Action, dated Jul. 14, 2015, 28 pages.
China Patent Application No. 201210063759.5, Notice of Allowance, dated Jun. 13, 2016, 6 pages.
China Patent Application No. 201210063759.5, Second Office Action, dated Jan. 12, 2016, 6 pages.
China Patent Application No. 201210063759.5, Supplementary Search, Mar. 24, 2016, 1 page.
Ciscor, Emergency Man Down Alarm System and Lone Worker Alarm System, Internet Archive Wayback Machine Feb. 7, 2004 to Apr. 1, 2016, 2 pages, http://web.archive.org/web/20040207202412/https://www.ciscor.com/sys/man_down_alarm_systems.html, Apr. 30, 2020.
Decision to grant a European patent dated Mar. 5, 2020 for EP Application No. 12152018.
English Translation of BR Office Action dated Dec. 16, 2019 for BR Application No. 102012001686.
English Translation of BR Office Action dated Jul. 19, 2019 for BR Application No. 102012001686.
Europe Application No. 12152018.3, Examination Report, dated Apr. 7, 2016, 7 pages.
Europe Application No. 12152018.3, Examination Report, dated Jun. 17, 2015, 5 pages.
Europe Application No. 12152018.3, Search Report, dated May 12, 2015, 3 pages.
European Patent Application No. 12152018.3, Communication pursuant to Article 94(3) EPC, dated Mar. 26, 2018, 6 pages.
European Search Report and Search Opinion Received for EP Application No. 12152018.3, dated May 12, 2015, 3 pages.
Final Rejection dated Apr. 12, 2017 for U.S. Appl. No. 13/015,327.
Final Rejection dated Jul. 23, 2013 for U.S. Appl. No. 13/015,327.
GCaptain.Com, PASS—Man Down Alarm, Internet Archive Wayback Machine, Oct. 27, 2007 to Jul. 5, 2008, Jun. 16, 2007, 5 pages, http://web.archive.org/web/20071027105233/http://gcaptain.com/maritime/blog/gcaptain-tip-confined-space-entry-with-pass-device/pass-man-down-alarm/, Apr. 30, 2020.
IN Office Action dated Nov. 20, 2018 for IN Application No. 219/DEL/2012.
Intention to grant dated Oct. 24, 2019 for EP Application No. 12152018.
Japan Patent Application No. 2012-011221, Decision to Grant, dated Jun. 25, 2015, 5 pages.
Japan Patent Application No. 2012-011221, Office Action, dated Dec. 11, 2014, 4 pages.
Japan Patent Application No. 2012-011221, Search Report by Registered Searching Organization, Dec. 9, 2014, 21 pages.
Loan Worker Safety Solutions, Internet Archive Wayback Machine, Oct. 20, 2008 to Feb. 15, 2015, Lone Worker Monitoring, 2 pages, web.archive.org/web/20081020202752/http://www.loneworkermonitoring.com/safetyline.htm, Apr. 30, 2020.
Motorola—ASTRO (Registered) MT 1500, Model 1 User Guide.
MSA the Safety Company, Altair (Registered) 4X Multigas Detector—Assemble-to-Order System and Pricing Guide—Prices effective Apr. 16, 2010.
MSA, ALTAIR 5 Multigas Detector, brochure, Copyright May 2009, MSAnet.com, 4 pages, http://media.msanet.com/na/usa/portableinstruments/ToxicGasandOxygenIndicators/Altair5/0802-46-MC_Altair5.pdf, Apr. 30, 2020.
MSA, motionSCOUT, Next Generation Stand-Alone Personal Alert Safety System, Internet Archive Wayback Machine, Feb. 21, 2013 to Nov. 17, 2017, s7d7.scene7.com, 3 pages, http://s7d9.scene7.com/is/content/minesafetyappliances/motionSCOUT%20Bulletin%20-%20GB.
MSA, The ALTAIR 4 Multigas Dectector, brochure, Copyright 2009, MSAnet.com, 4 pages, http://media.msanet.com/na/usa/portableinstruments/ToxicGasandOxygenIndicators/Altair4/0802-50-ALTAIR4.pdf, Apr. 30, 2020.
Non-Final Rejection dated Dec. 4, 2013 for U.S. Appl. No. 13/015,327.
Non-Final Rejection dated Dec. 14, 2016 for U.S. Appl. No. 13/015,327.
Non-Final Rejection dated Mar. 29, 2013 for U.S. Appl. No. 13/015,327.

(56) References Cited

OTHER PUBLICATIONS

Notice of Allowance and Fees Due (PTOL-85) dated Feb. 4, 2020 for U.S. Appl. No. 13/015,327.
Office Action received for European Application No. 12152018.3, dated Apr. 7, 2016, 7 pages.
Office Action received for European Application No. 12152018.3, dated Jun. 17, 2015, 5 pages.
Office Action received for European Application No. 12152018.3, dated Mar. 26, 2018, 6 pages.
PASS device—Wikipedia, the free encyclopedia, Internet Archive Wayback Machine, Dec. 15, 2005 to Apr. 25, 2020, Wikimedia Foundation, web.archive.org/web/20100302153839/http://en.wikipedia.org/wiki/PASS_device, Apr. 30, 2020.
Russian Patent Application No. 2012103389, Notice of Allowance, dated Sep. 9, 2016, 15 pages.
Russian Patent Application No. 2012103389, Office Action, dated Feb. 9, 2016, 7 pages.
Summons to Attend Oral Proceeding for EP Application No. 12152018.3, May 24, 2019.
United Arab Emirates Application No. 00812012, Examination Report, dated Jul. 24, 2017, 5 pages.
United Arab Emirates Application No. 00812012, Search Report, dated Jul. 24, 2017, 6 pages.
www.trackandlocate, Man Down System, Man Down Solutions, SOS Tracking Solutions—Track and Locate, Internet Archive Wayback Machine, Mar. 30, 2009 to Mar. 25, 2015, 2 pages, https://web.archive.org/web/20090330024043/http://www.trackandlocate.net/man-down-system.html, Apr. 30, 2020.
CA Notice of Allowance dated Sep. 23, 2020 for CA Application No. 2765328, 1 page.
Extended European Search Report and Search Opinion dated Sep. 28, 2020 for EP Application No. 20165730, 12 pages.
U.S. Appl. No. 13/015,327, filed Jan. 27, 2011, Patented, U.S. Pat. No. 10,685,554.

\* cited by examiner

SYSTEMS AND METHODS FOR ROBUST MAN-DOWN ALARMS

CROSS-REFERENCE TO RELATED APPLICATIONS

This application is a division of, and claims priority to, and the benefit of, U.S. Non-Provisional patent application Ser. No. 13/015,327, filed Jan. 27, 2011 and entitled "Systems and Methods for Robust Man-Down Alarms," the entire contents of which are hereby incorporated herein by reference in their entirety for all purposes.

FIELD

The present invention relates generally to alarm reporting. More particularly, the present invention relates to systems and methods for detecting, generating, and reporting robust man-down alarms.

BACKGROUND

Gas detectors are generally used by workers who are working in a potentially dangerous area where gas hazards may be present. These types of gas detectors can be designed to alert a user of the detector when a hazardous gas has been detected, but while the hazardous gas concentration is still low enough for the user to take action. Thus, a user can identify an impending hazard and remove himself from an area with a growing hazard before the user is incapacitated from the gas.

However, in some cases workers cannot remove themselves from a hazardous area on their own. For example, a worker may be exposed to a rapid release of a hazardous gas and be incapacitated before removing himself from the hazardous area. In these types of cases, it would be desirable to alert a rescue team or other authority that the worker is incapacitated.

Some systems and methods for reporting a man-down alarm are known in the art, but these known systems and methods have significant limitations. For example, some industrial radios known in the art incorporate a man-down alarm in which the user presses a button on the radio when he is in distress. This system enables a worker to signal for help and for a central office to arrange a rescue. However, this system presents at least three significant limitations.

First, this system does not function when the worker is already unconscious or otherwise incapacitated. Second, this system does not indicate who has triggered the alarm. And third, this system is prone to false alarms when an alert button is inadvertently pressed.

Some gas detectors known in the art include both a motion detector and alarm capability. When enabled, the gas detector generates an alarm if the detector has not moved for at least a predetermined period of time, for example, 30 seconds. Thus, in these types of detectors, the lack of movement indicates an incapacitated user, and an alarm is generated. However, this system presents at least two limitations.

First, there may be cases in which a user has not moved for the predetermined period of time, but is not unconscious or otherwise incapacitated. In these cases, the detector will generate a false alarm. And second, a man-down alarm generated by this system will be strictly local, and no remote call for assistance will be sent.

There is thus a continuing, ongoing need for improved systems and methods for detecting, generating, and reporting robust man-down alarms. Preferably, these systems and methods reduce false alarms, determine the likelihood of a man-down event occurring, and generate a remote alarm.

DESCRIPTION OF THE PREFERRED EMBODIMENTS

Figure 1:
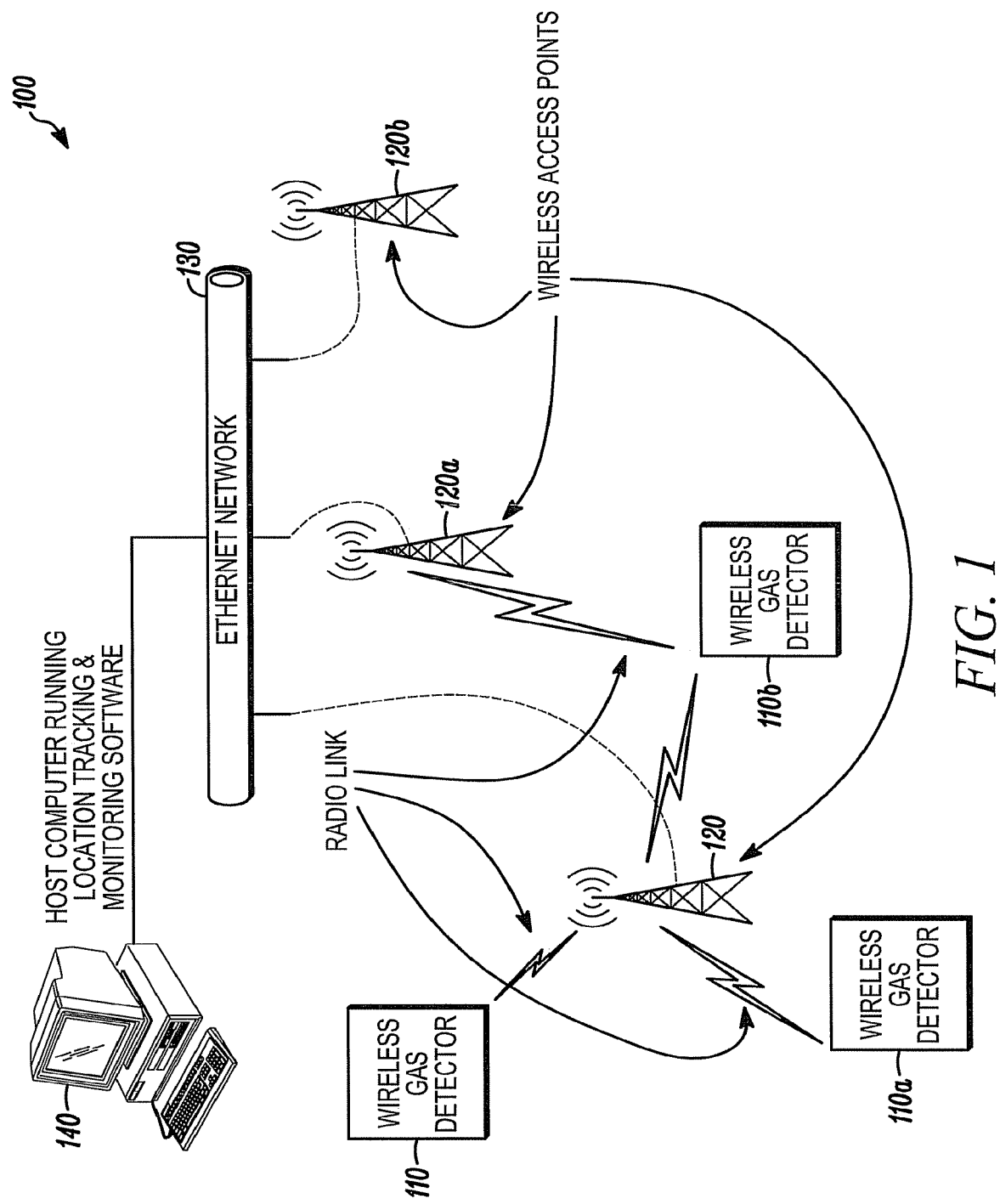
FIG. 1 is an overall diagram of a system for detecting, generating, and reporting a robust man-down alarm in accordance with the present invention.

While this invention is susceptible of an embodiment in many different forms, there are shown in the drawings and will be described herein in detail specific embodiments thereof with the understanding that the present disclosure is to be considered as an exemplification of the principles of the invention. It is not intended to limit the invention to the specific illustrated embodiments.

Embodiments of the present invention include improved systems and methods for detecting, generating, and reporting robust man-down alarms. Such systems and methods can reduce false alarms, determine the likelihood of a man-down event occurring, and generate a remote alarm.

False alarms can be reduced in at least two ways. First, in embodiments of the present invention, information from several sources can be correlated. For example, information from a motion sensor can be correlated with information from a gas and/or temperature sensor. When this information is correlated, systems and methods in accordance with the present invention can determine whether a man-down event is likely to have occurred before generating an alarm.

Second, in embodiments of the present invention, a detector can include two-way communication capabilities. When a lack of movement is detected at a detector, systems and methods of the present invention can transmit a lack of movement alert to a remote location. Then, the remote location can transmit a message back to the detector to inquire about the health of the user of the detector. If the alert location receives a response indicating that the user is not in danger or peril, then systems and methods in accordance with the present invention can determine that a false alarm was detected. However, if the alert location does not receive a response indicating that the user is not in danger or peril, then systems and methods in accordance with the present invention can determine that a man-down event is likely and can instruct an emergency response team to rescue the user.

In accordance with the present invention, the likelihood of a man-down alarm occurring can be determined. For example, information from multiple detectors in the same area can be correlated to determine the likelihood of a legitimate man-down event occurring. When a plurality of detectors are in the same area, when at least one of the detectors detect a lack of movement for a predetermined period of time, and when all, substantially all, a majority, or even one of the detectors detect a high level of a hazardous gas, systems and methods in accordance with the present invention can determine that a legitimate man-down event is likely.

Similarly, when a single detector detects a lack of movement for a predetermined period of time and all of the other detectors in the same area are detecting normal movement, but no hazardous gas has been detected, systems and methods in accordance with the present invention can determine that a user of the single detector is simply sitting still and is not unconscious or otherwise incapacitated. Under these circumstances, systems and methods of the present invention can determine that a man-down alarm is not appropriate.

In accordance with the present invention, a remote alarm can also be generated. For example, a detector in accordance with the present invention can communicate with a central station. When the central station receives communication that a user of the detector is unconscious or otherwise incapacitated, and when the central station determines that there is no false alarm, then the central station can transmit communication to an emergency rescue team to assist the user. Similarly, when the central station receives communication that a man-down event is likely, then the central station can transmit communication to the emergency response team.

FIG. 1 is an overall diagram of a system 100 for detecting, generating, and reporting a robust man-down alarm, in accordance with the present invention. As seen in FIG. 1, a system 100 in accordance with the present invention can include at least one detector 110 and a central station 140.

The system can include one or a plurality of detectors 110, for example, 110a and 110b. In embodiments of the present invention, the detectors 110 can be gas detectors, or any other detector as would be known and desired by one of ordinary skill in the art. For example, the detectors 110 could include smoke or fire detectors.

In further embodiments of the present invention, the detectors 110 can be wireless or wired. For example, as seen in FIG. 1, when the detectors 110, 110a, 110b are wireless, the detectors 110, 110a, 110b can communicate with the central station 140 via a wireless network infrastructure, including access points 120, 120a, 120b, and a Wide Area Network (WAN) or a Local Area Network (LAN), such as, for example, an Ethernet network 130. Wireless detectors 110, 110a, 110b can communicate with wireless access points 120, 120a, 120b via, for example, radio signals.

The central station 140 can include a host computer, for example a personal computer, and can receive information reported from the detectors 110, 110a, 110b. In embodiments of the present invention, the central station 140 can include a programmable processor and associated control circuitry for running software, stored on a local computer readable medium, as would be understood by those of ordinary skill in the art.

Figure 2:
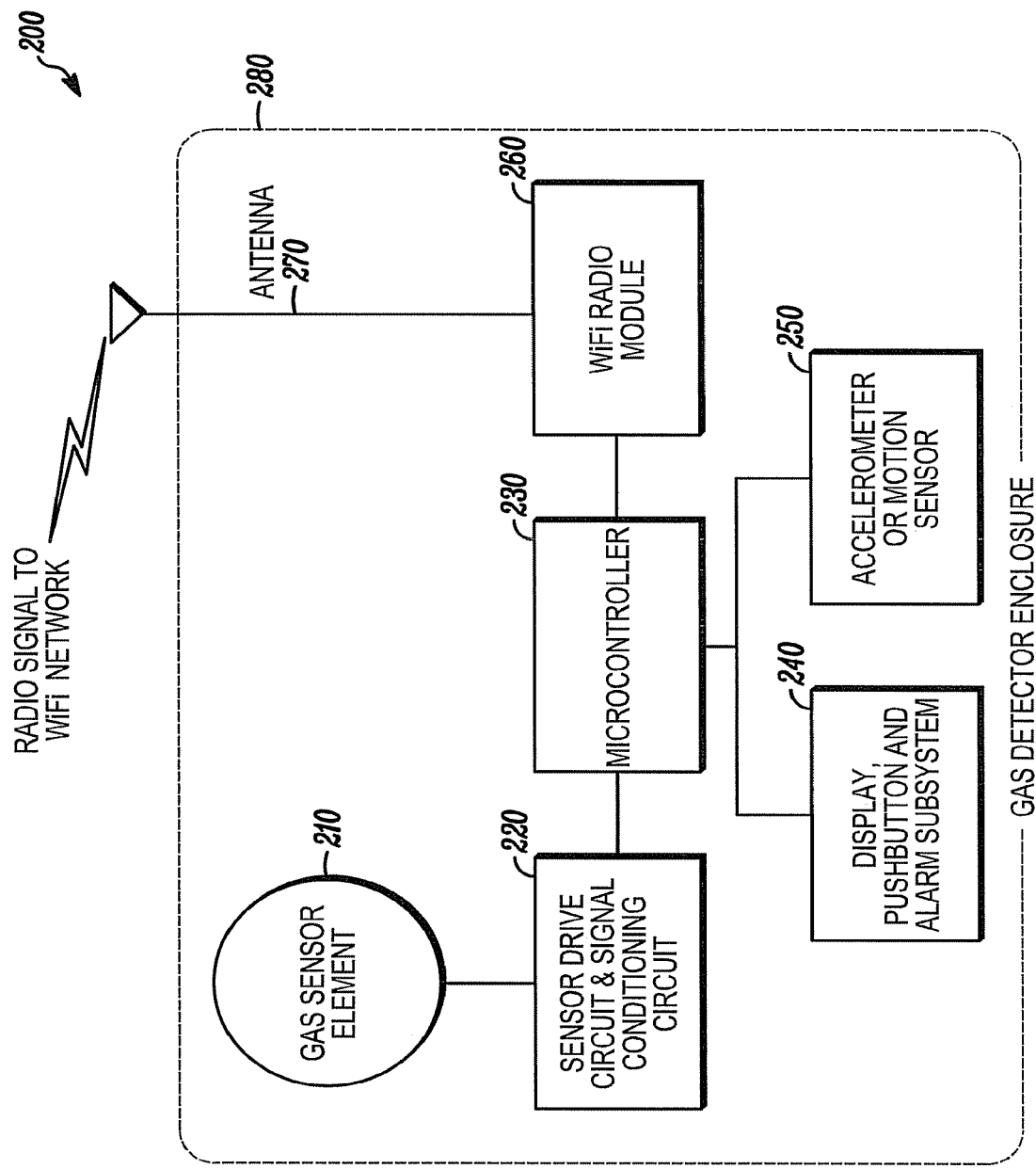
FIG. 2 is a block diagram of a detector in accordance with the present invention.

FIG. 2 is a block diagram of a detector 200 in accordance with the present invention. As seen in FIG. 2, the detector 200 is a wireless gas detector. However, as explained above, detectors in accordance with the present invention are not so limited.

The detector 200 can include a gas sensor element 210, a sensor drive circuit and signal conditioning circuit 220, a microcontroller 230, a display, pushbutton and alarm subsystem 240, an accelerometer or motion sensor 250, a radio module 260, and an antenna 270. The radio module 260 can support any number of radio communications such as, for example, Wi-Fi, ISA100, GPRS, EDGE, 3G, 4G, 900 MHz point to point, WAN, and the like. Each of these components can be enclosed in a housing 280. In some embodiments, at least a portion of the antenna 270 can protrude from the housing 280.

In accordance with the present invention, the gas sensor element 210 can detect a presence of a predetermined gas or gases in the ambient atmosphere. For example, the gas sensor element 210 can detect that the amount of a hazardous gas in the ambient atmosphere has reached a predetermined threshold.

When conditions are met, the gas sensor element 210 can transmit a signal to the sensor drive circuit and signal conditioning circuit 220, which can transmit a signal to the microcontroller 230. When the received signal indicates a presence of a predetermined gas in the ambient atmosphere or indicates that the amount of a hazardous gas in the ambient atmosphere has reached a predetermined threshold, the microcontroller 230 can generate a gas alarm signal. The microcontroller 230 can then transmit the gas alarm signal to the radio module 260, and the gas alarm signal can be transmitted via the antenna 270. For example, the antenna 270 can transmit the gas alarm signal to a central monitoring station. The display, pushbutton and alarm subsystem 240 can receive inputs from a user of the detector 200.

In embodiments of the present invention, the accelerometer or motion sensor 250 can determine movement of the detector 200 and therefore, movement of a user associated with the detector 200. When the sensor 250 determines that the user has not moved for a predetermined period of time, the sensor 250 can send a signal to the microcontroller 230, and the microcontroller 230 can generate a man-down signal. The microcontroller 230 can then transmit the man-down signal to the radio module 260, and the man-down signal can be transmitted via the antenna 270. For example, the antenna 270 can transmit the man-down signal to a central monitoring station.

Figure 3:
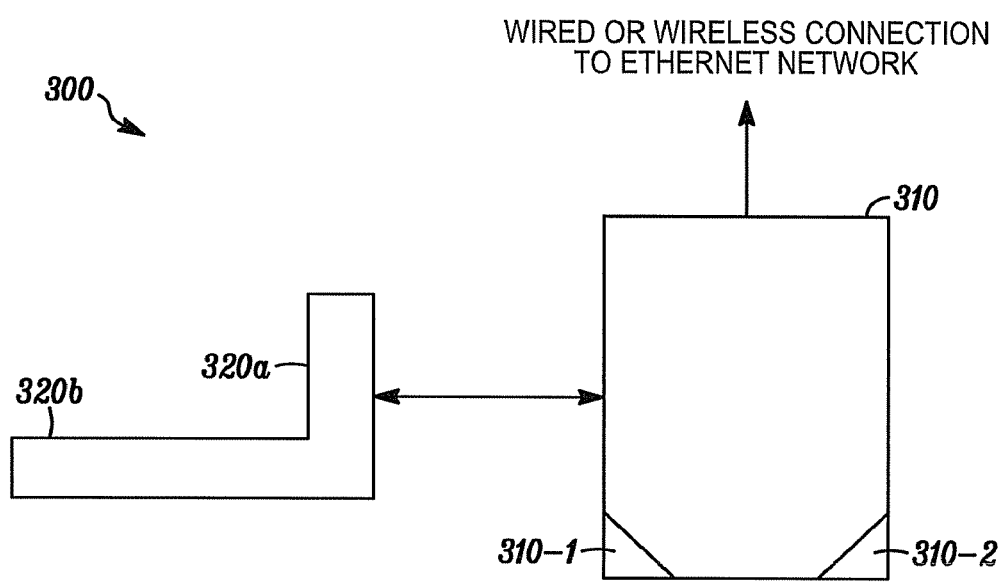
FIG. 3 is a block diagram of a central station in accordance with the present invention.

FIG. 3 is a block diagram of a central station 300 in accordance with the present invention. The central station 300 can communicate with and receive information from remote detectors.

As seen in FIG. 3, the central station 300 can include a control unit 310 that can be in wired or wireless communication with detectors via a Wide Area Network (WAN) or a Local Area Network (LAN, such as, for example, an Ethernet network. The control unit 310 can be implemented with one or more programmed processors 310-1 and executable control software 310-2 as would be understood by those of ordinary skill in the art.

The central station 300 can also include a computer driven display unit 320a as well as one or more input devices 320b, which could include keyboards, track balls and the like all without limitation. The control unit 310 can communicate with a user at the central station 310 via the display unit 320a and a graphical user interface that can provide status information to the user and receive information from the user.

The central station 300 can use information received from a detector in several ways. For example, the central station 300 can inform a user local to the central station 300 that an alarm at the detector, for example, a gas alarm or a man-down alarm, has occurred. The user at the central station 300 can then attempt to contact the remote user of the detector to determine if the user is in distress or to determine if it is appropriate to initiate a rescue operation. In embodiments of the present invention, the remote user of the detector need not be conscious or capable of any action for the user to be rescued.

The central station 300 can also use information received from a detector to determine the location of a detector indicating alarm. Systems and methods for determining the location of a remote device are known in the art and so will not be described in detail here. However, it is to be understood that the central station 300 can determine the location of a detector from information sent by the detector to the central station 300.

Figure 5:
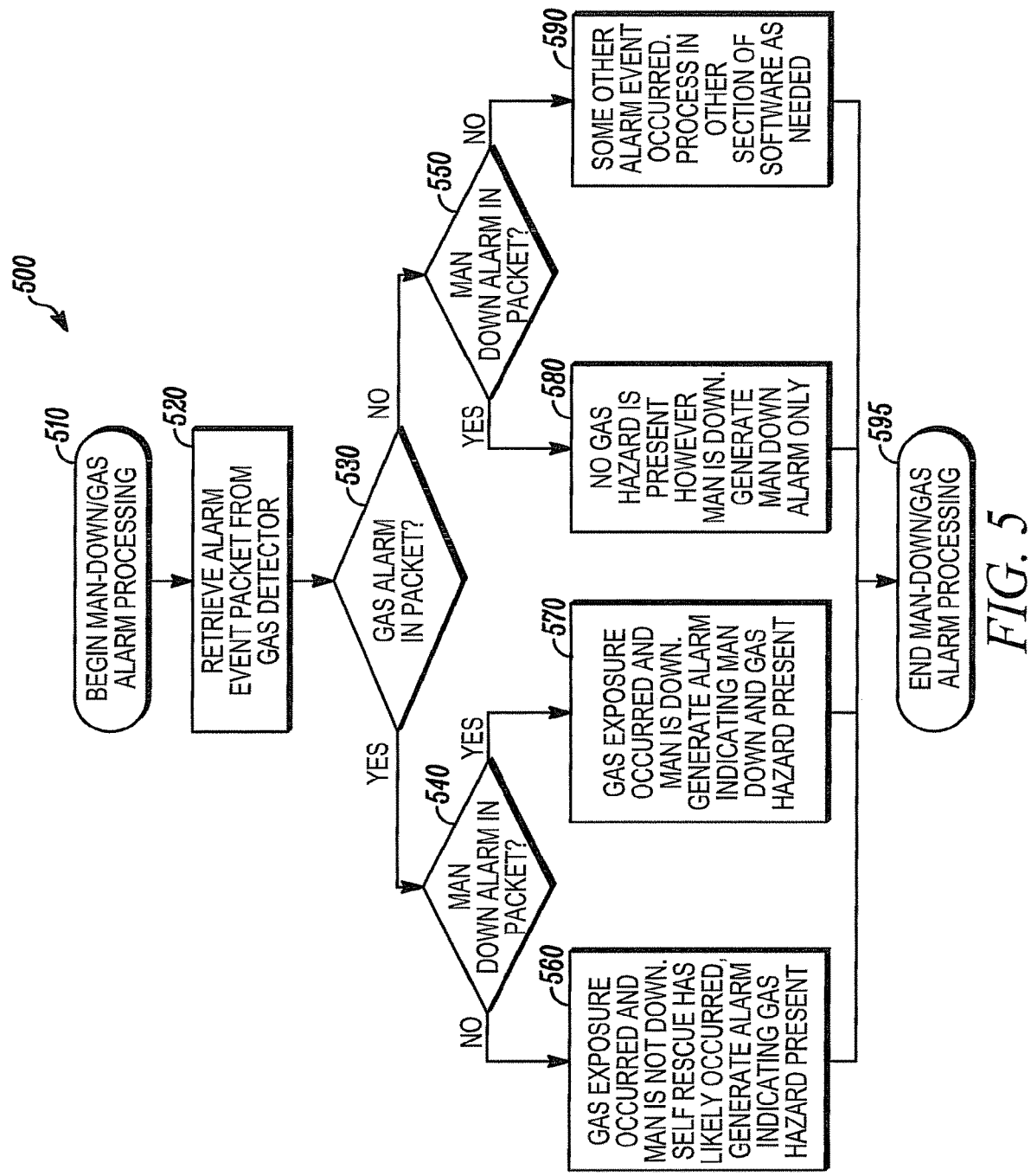
FIG. 5 is flow diagram of a method of tracking and monitoring alarm signals in accordance with the present invention.
Figure 6:
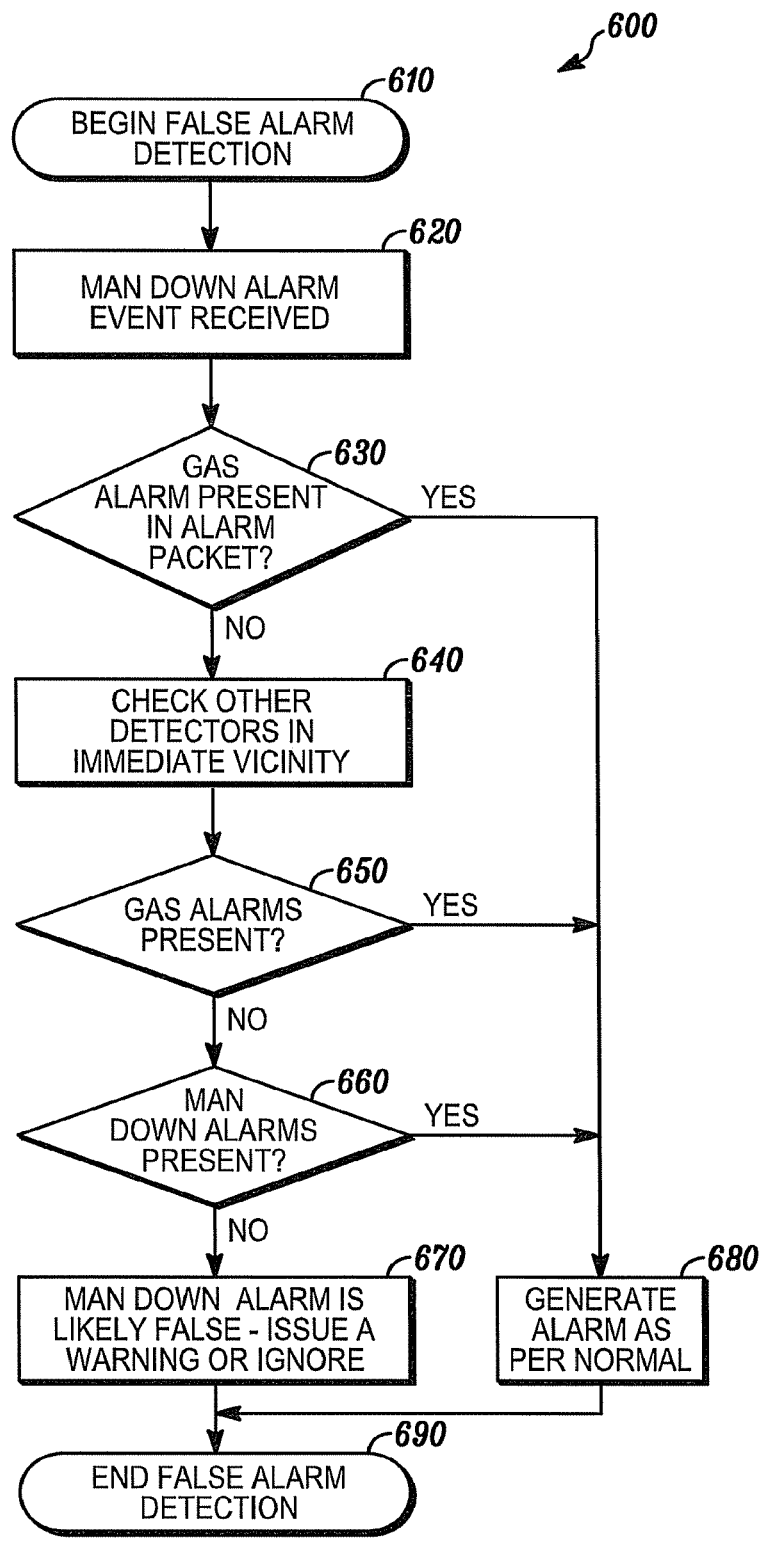
FIG. 6 is a flow diagram of a method of detecting for false alarms in accordance with the present invention.

Furthermore, the central station 300 can use information received from a detector to determine appropriate courses of action given the circumstances. For example, the central station 300 can receive location information as well as information related to gas alarms and man-down alarms from a detector. The central station 300 can use this information to determine the likelihood of the presence of a hazardous gas and the likelihood that the user of the detector is unconscious. The central station 300 can also use this information to generate gas alarms and/or man-down alarms and to determine false alarms. Methods of making these determinations are shown in FIG. 5 and FIG. 6 and will be described in more detail herein.

Figure 4:
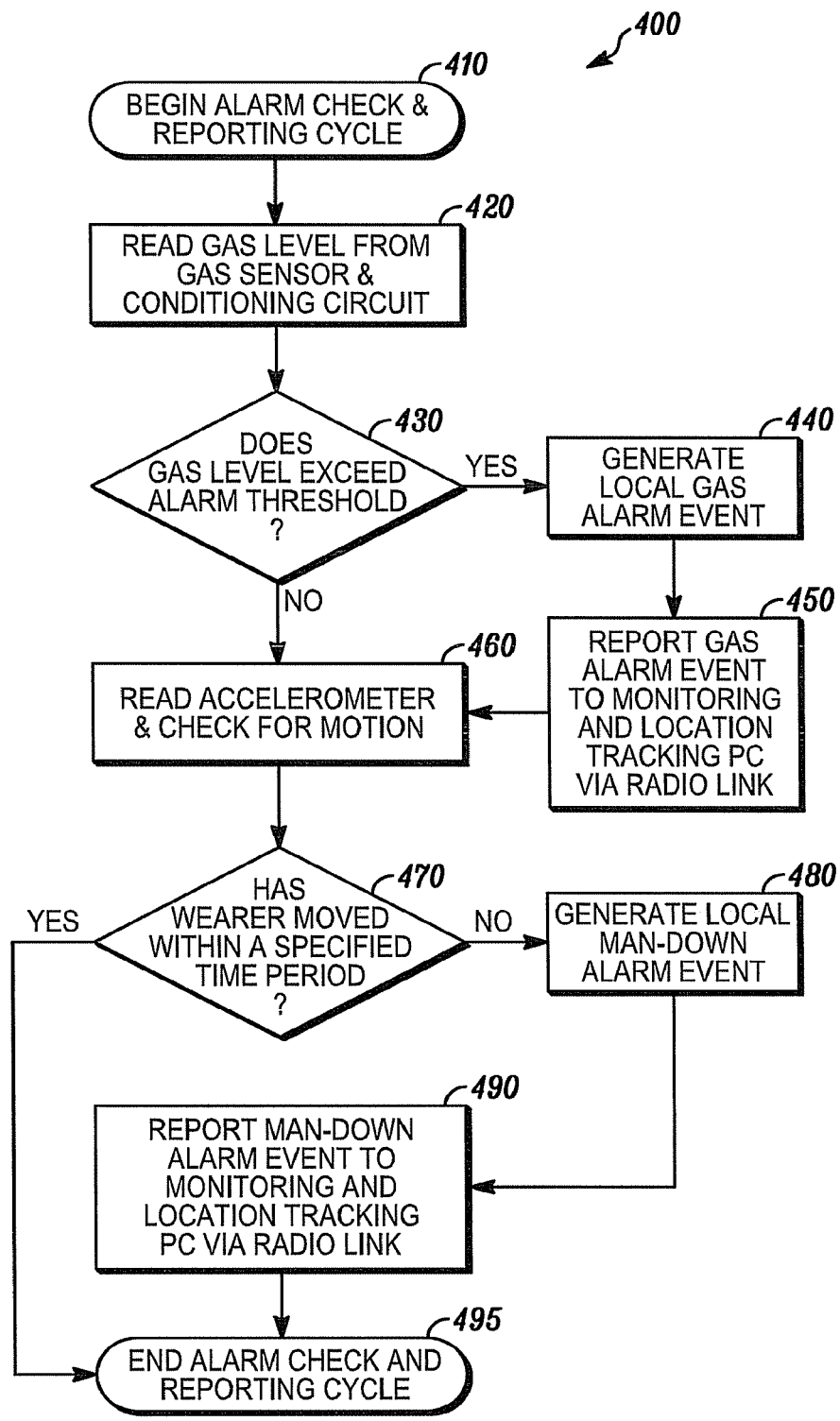
FIG. 4 is a flow diagram of a method of detecting, generating, and reporting a robust man-down alarm in accordance with the present invention.

FIG. 4 is a flow diagram of a method 400 of detecting, generating, and reporting a robust man-down alarm in accordance with the present invention. In embodiments of the present invention, a detector, for example, the detector 200 shown in FIG. 2 can execute the method 400.

The method 400 can be executed at predetermined regular intervals, as required, to detect the presence of a hazardous gas. For example, the method 400 can be executed once per second.

The method 400 can begin the alarm check and reporting cycle as in 410, and a gas level can be read from a gas sensor and a conditioning circuit as in 420. Then, the method 400 can determine if the gas level exceeds an alarm threshold as in 430. For example, the alarm threshold could be 10 ppm H2S. If the gas level does not exceed an alarm threshold, then an accelerometer can be read and checked for motion as in 460.

However, if the gas level does exceed an alarm threshold, then a local gas alarm can be generated as in 440, and the gas alarm can be reported to a central station as in 450. For example, the gas alarm can be reported to a remote personal computer that monitors and tracks location. In embodiments of the present invention, the gas alarm can be reported from the detector via radio signals.

After a gas alarm is reported to the central station as in 450, an accelerometer can be read and checked for motion as in 460. Then, the method 400 can determine if a user has moved within a predetermined period of time as in 470. For example, the predetermined period of time could be 120 seconds. If the user has moved within the predetermined period of time, then the method 400 can end the alarm check and reporting cycle as in 495.

However, if the user has not moved within the predetermined period of time, then a local man-down alarm can be generated as in 480, and the man-down alarm can be reported to a central station as in 490. For example, a man-down alarm can be reported to a remote personal computer that monitors and tracks location. In embodiments of the present invention, the man-down alarm can be reported from the detector via radio signals.

After a man-down alarm is reported, the method 400 can end the alarm check and reporting cycle as in 495 and begin anew the alarm check and reporting cycle as in 410.

FIG. 5 is flow diagram of a method 500 of tracking and monitoring alarm signals in accordance with the present invention. In embodiments of the present invention, a central station, for example, the central station 140 shown in FIG. 1 or the central station 300 shown in FIG. 3, can execute the method 500.

As explained above, the central station 140 or 300 can include programmed processors and executable control software. In embodiments of the present invention, the processors, software, and any associated control circuitry can track the location of and monitor information reported from associated detectors, for example, wireless gas detectors.

The method 500 can begin the man-down alarm and gas alarm processing as in 510, and an alarm event packet can be retrieved from a gas detector as in 520. Then, the method 500 can determine if the alarm packet includes a gas alarm as in 530.

If the method 500 determines that the alarm packet does include a gas alarm as in 530, then the method 500 can proceed to determine if the alarm packet includes a man-down alarm as in 540. However, if the method 500 determines that the alarm packet does not include a gas alarm as in 530, then the method 500 can proceed to determine if the alarm packet includes a man-down alarm as in 550. Determining if the alarm packet includes a man-down alarm as in 540 is different from determining if the alarm packet includes a man-down alarm as in 550 because of subsequent determinations made by the method 500.

If the method 500 determines that the alarm packet does not include a man-down alarm as in 540, then the method 500 can determine that gas exposure has occurred, but that the user is not unconscious or otherwise incapacitated as in 560. The method 500 can also determine that self-rescue has likely occurred as in 560, and an alarm can be generated indicating the presence of a hazardous gas as in 560. Then, the method can end the man-down alarm and gas alarm processing as in 595.

If the method 500 determines that the alarm packet does include a man-down alarm as in 540, then the method 500 can determine that gas exposure has occurred and that the user is unconscious or otherwise incapacitated as in 570. One or more alarms can also be generated indicating that a hazardous gas is present and that a user is incapacitated as in 570. Then, the method can end the man-down alarm and gas alarm processing as in 595.

If the method determines that the alarm packet includes a man-down alarm as in 550, then the method 500 can determine that no hazardous gas is present, but that a user is unconscious or otherwise incapacitated as in 580. An alarm can also be generated indicating that a user is incapacitated as in 580. Then, the method can end the man-down alarm and gas alarm processing as in 595.

If the method determines that the alarm packet does not include a man-down alarm as in 550, then the method 500 can determine that some other alarm event occurred as in 590. Then, the method can end the man-down alarm and gas alarm processing as in 595.

FIG. 6 is a flow diagram of a method 600 of detecting for false alarms in accordance with the present invention. In embodiments of the present invention, a central station, for example, the central station 140 shown in FIG. 1 or the central station 300 shown in FIG. 3 can execute the method 600.

The method 600 can begin the false alarm detection processing as in 610, and a man-down alarm can be received from a first detector as in 620. The, the method 600 can determine if the alarm packet from the first detector includes a gas alarm as in 630.

If the method 600 determines that the alarm packet from the first detector includes a gas alarm as in 630, then an alarm can be generated as in 680, and the method 600 can end the false alarm detection processing as in 690.

However, if the method 600 determines that the alarm packet from the first detector does not include a gas alarm as in 630, then a plurality of other detectors in the vicinity of the first detector can be checked as in 640. Then, the method 600 can determine if gas alarms are present in alarm packets received from the plurality of other detectors as in 650.

If the method 600 determines that gas alarms are present in alarm packets received from the plurality of other detectors as in 650, then an alarm can be generated as in 680, and the method 600 can end the false alarm detection processing as in 690. However, if the method 600 determines that gas alarms are not present in alarm packets received from the plurality of other detectors as in 650, then the method 600 can determine if man-down alarms are present in alarm packets received from the plurality of other detectors as in 660.

If the method 600 determines that man-down alarms are present in alarm packets received from the plurality of other detectors as in 660, then an alarm can be generated as in 680, and the method 600 can end the false alarm detection processing as in 690. However, if the method 600 determines that man-down alarms are not present in alarm packets received from the plurality of other detectors as in 660, then the method 600 can determine that the man-down alarm received from the first detector as in 620 is false. The method can issue a warning regarding the false alarm or simply ignore the false alarm as in 670. Then, the method 600 can end the false alarm detection processing as in 690.

In embodiments of the present invention, the method 600 shown in FIG. 6 can be executed whenever a man-down alarm is received from a detector. For example, when the central station 140 receives a man-down alarm from any detector 110, 110*a*, 110*b* in the system 100, the central station 140 can execute the method 600 to determine if the alarm is a false alarm.

When evaluating, as in 640, 650, and 660, alarm packets from the plurality of other detectors in the vicinity of the first detector, some or all of the plurality of other detectors in the vicinity can be evaluated. For example, in embodiments of the present invention, all, substantially all, a majority, or even one of the plurality of other detectors can be evaluated.

In some embodiments, all, substantially all, a majority, or only one of the plurality of other detectors must transmit an alarm packet including a gas alarm for the method 600 to determine the presence of gas alarms from the plurality of other detectors as in 650. Similarly, in some embodiments, all, substantially all, a majority, or only one of the plurality of other detectors must transmit an alarm packet including a man-down alarm for the method 600 to determine the presence of man-down alarms from the plurality of other detectors as in 660.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

From the foregoing, it will be observed that numerous variations and modifications may be effected without departing from the spirit and scope of the invention. It is to be understood that no limitation with respect to the specific system or method illustrated herein is intended or should be inferred. It is, of course, intended to cover by the appended claims all such modifications as fall within the spirit and scope of the claims.

What is claimed is:

1. A man-down device configured to be carried by a user, said man-down device comprising:
    a motion sensor configured to sense a magnitude of motion of the man-down device; and
    control circuitry configured to be in operable communication with one or more of a gas detector or one or more second man-down devices,
    wherein the control circuitry is configured to:
        determine, based at least upon one or more signals received from the motion sensor, a period in which the man-down device is motionless for greater than an identified period of time,
        in an instance in which the man-down device is motionless for greater than said identified period of time, correlate said period in which the man-down device is motionless for greater than the identified period of time with one or more other signals from one or more of the gas detector or the one or more second man-down devices, the one or more other signals being indicative of at least one of: an ambient temperature, an ambient gas concentration, a magnitude of motion, a smoke concentration, or a man-down alarm, and
        determine, based at least upon said correlating, a probability that the period in which the man-down device is motionless for greater than the identified period of time is indicative of a false alarm.

2. The man-down device of claim 1, further comprising:
    one or more ambient sensors configured to sense a temperature, a gas concentration, or a smoke concentration in an ambient environment surrounding the man-down device.

3. The man-down device of claim 1, wherein the control circuitry is further configured to:
    determine a location of the man-down device.

4. The man-down device of claim 1, wherein the motion sensor comprises an accelerometer.

5. The man-down device of claim 1, further comprising a temperature sensor.

6. A method comprising:
    monitoring, using a motion sensor, a magnitude of motion of a man-down device;
    in an instance in which the man-down device is determined to be motionless for longer than an identified duration of time, correlating said period in which the man-down device is motionless for greater than the identified period of time with one or more other signals from one or more of the gas detector or the one or more second man-down devices, the one or more other signals being indicative of at least one of: an ambient temperature, an ambient gas concentration, a magnitude of motion, a smoke concentration, or a man-down alarm; and
    determining, based at least upon said correlating, a probability that the period in which the man-down device is motionless for greater than the identified period of time is indicative of a false alarm.

7. The method of claim 6, further comprising:
    in an instance in which said probability is above a predetermined threshold, determining the man-down alarm is a false alarm, and not sending a notification of a man-down event to an emergency response station.

8. The method of claim 6, further comprising:
in an instance in which said man-down alarm is above a predetermined threshold, determining the man-down alarm is not a false alarm; and
sending a notification of a man-down event to an emergency response station.

9. The method of claim 8, further comprising:
determining a location of said man-down device; and
transmitting said location, with said notification of said man-down event to the emergency response station.

10. A man-down device comprising:
a motion sensor configured to sense a magnitude of motion of the man-down device;
an ambient sensor configured to sense a temperature, a gas concentration, or a smoke concentration in an ambient environment about the man-down device; and
control circuitry configured to:
   determine, based at least upon one or more signals received from the motion sensor, a period in which the man-down device is motionless for greater than an identified period of time,
   in an instance in which the man-down device is motionless for greater than said identified period of time, correlate said period in which the man-down device is motionless for greater than the identified period of time with the temperature, the gas concentration, or the smoke concentration sensed by the ambient sensor, and
   determine, based at least upon said correlating, a probability that the period in which the man-down device is motionless for greater than the identified period of time is indicative of a false alarm.

11. The man-down device of claim 10, further comprising:
a receiver configured to receive, from one or more gas detectors or one or more second man-down devices, one or more other signals,
wherein said determination of the probability further comprises correlating the one or more other signals with the period in which the man-down device is motionless for greater than the identified period of time with the temperature, the gas concentration, or the smoke concentration sensed by the ambient sensor of the man-down device.

12. The man-down device of claim 10, wherein the control circuitry is further configured to:
determine a location of the man-down device.

13. The man-down device of claim 10, wherein the motion sensor comprises an accelerometer.

* * * * *